US012534259B2

(12) United States Patent
Giansante

(10) Patent No.: US 12,534,259 B2
(45) Date of Patent: Jan. 27, 2026

(54) METHOD AND APPARATUS FOR FORMING GROUPS OF ABSORBENT SANITARY ARTICLES

(71) Applicant: Fameccanica.Data S.p.A., San Giovanni Teatino Chieti (IT)

(72) Inventor: Antonio Giansante, San Giovanni Teatino Chieti (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 0 days.

(21) Appl. No.: 18/584,029

(22) Filed: Feb. 22, 2024

(65) Prior Publication Data

US 2024/0286784 A1 Aug. 29, 2024

(30) Foreign Application Priority Data

Feb. 24, 2023 (IT) ........................ 102023000003255

(51) Int. Cl.

| | |
|---|---|
| ***B65B 63/04*** | (2006.01) |
| ***A61F 13/15*** | (2006.01) |
| ***A61F 13/551*** | (2006.01) |
| ***B65B 35/50*** | (2006.01) |
| ***B65B 65/00*** | (2006.01) |

(52) U.S. Cl.

CPC ........ *B65B 63/04* (2013.01); *A61F 13/15747* (2013.01); *A61F 13/15764* (2013.01); *A61F 13/55145* (2013.01); *B65B 35/50* (2013.01); *B65B 65/003* (2013.01)

(58) Field of Classification Search

CPC .......... A61F 13/15747; A61F 13/15764; A61F 13/15804; A61F 13/55145; A61F 2013/15821; B65B 35/42; B65B 35/44; B65B 35/50; B65B 63/04; B65B 63/045; B65B 65/003

See application file for complete search history.

(56) References Cited

U.S. PATENT DOCUMENTS

| | | | | |
|---|---|---|---|---|
| 8,496,637 | B2 | 7/2013 | Hundorf et al. | |
| 2008/0312624 | A1* | 12/2008 | Hundorf | A61F 13/55115 206/440 |
| 2020/0237572 | A1* | 7/2020 | Giffey | A61F 13/15747 |
| 2022/0074125 | A1* | 3/2022 | Chae | D06F 89/02 |

FOREIGN PATENT DOCUMENTS

| | | | | |
|---|---|---|---|---|
| EP | 3685812 | A1 | 7/2020 | |
| WO | 2008155702 | A1 | 12/2008 | |
| WO | WO-2013136252 | A2 * | 9/2013 | B65D 85/07 |

OTHER PUBLICATIONS

IT Search Report dated Aug. 7, 2023. 6 pages.

* cited by examiner

*Primary Examiner* — Himchan Song
(74) *Attorney, Agent, or Firm* — RMCK Law Group PLC

(57) ABSTRACT

A method for folding absorbent sanitary articles, wherein a plurality of absorbent sanitary articles advancing at a first speed are alternately routed towards at least two folding lines, are slowed down to a second speed less than the first speed, are folded while advancing at the second speed and are overlapped with each other so as to form groups of articles, each of which comprises at least two folded absorbent sanitary articles overlapped with each other.

8 Claims, 4 Drawing Sheets

14
16
V1
MD 18
20

V2

60
58

METHOD AND APPARATUS FOR FORMING GROUPS OF ABSORBENT SANITARY ARTICLES

CROSS-REFERENCE TO RELATED APPLICATION

This application claims priority to Italian Patent Application No. 102023000003255 filed Feb. 24, 2023. The disclosure of the above application is incorporated herein by reference in its entirety.

FIELD OF THE INVENTION

The present invention generally relates to packaging of absorbent sanitary articles.

In particular, the invention refers to the formation of groups of absorbent sanitary articles folded around one or two transverse folding lines at the end of a production line and upstream of a packaging machine.

The invention was developed in particular with a view to its application to the field of female sanitary pads, such as for example panty liners, light inco, or the like.

The invention, however, is not limited to this specific field and can be used in all cases where there is a need to form groups of absorbent sanitary articles folded around one or two transverse folding lines.

DESCRIPTION OF THE PRIOR ART

Some absorbent sanitary articles, such as female sanitary pads, are often individually packaged in individual pouch-like packaging.

The individual packaging of absorbent sanitary articles may be carried out by enclosing the individual absorbent sanitary articles between two flexible sheets overlapped on each other, which enclose sandwich-like a respective absorbent sanitary article and joined together at their edges by adhesive.

Solutions are also known wherein each absorbent sanitary article is closed in a casing made up of a single sheet of flexible material folded to form two flaps joined together at their edges by adhesive.

The packages may be made up of sheets of plastic material, for example, polyethylene, or paper material.

Before packaging, the absorbent sanitary articles are often folded into two or three. This folding is carried out by folding the absorbent sanitary articles around one or two lines transverse with respect to a longitudinal axis of the article. Female sanitary pads are often folded into three overlapping parts.

EP-A-2157952, FIG. 18, describes a folding apparatus for tri-folding disposable absorbent articles, wherein the absorbent articles are inserted between two opposing belts by folding blades which impact the articles transversally along folding lines. In a first folding assembly, the sanitary articles are folded for approximately one third of their length. The partially folded articles are sent to a second folding assembly which folds the remaining part, producing a tri-folded sanitary article made up of three overlapping layers.

In modern machines for producing absorbent sanitary articles, the articles move at extremely high speeds. For example, in the case of absorbent sanitary articles with a length in the machine direction of 300 mm and with a machine operating at a rate of 1000 pieces per minute, the articles move at a speed of 300 m/min and each of the folding blades impacts the sanitary articles with a frequency of 1000 strokes per minute.

Due to the high linear speed of the absorbent sanitary articles upon impact with the folding blades, there is a risk of damage to the articles. The frequency of damage to the absorbent sanitary articles increases as a function of the speed of advancement of the articles.

In solutions according to the prior art, folded absorbent sanitary articles are usually slowed down before being packaged. This slowdown may be obtained by exploiting the difference in speed between a first pair of belts moving at the speed of the production machine and a second pair of belts moving at the speed of the packaging machine, usually equal to approximately half the speed of the production machine. Slowing down the folded absorbent sanitary articles may lead to production stops, for example, due to uncontrolled movement of the folded articles, resulting in jams.

With solutions according to the prior art it is generally not possible to manage the packaging of two folded products overlapping each other.

OBJECT AND SUMMARY OF THE INVENTION

The object of the present invention is to provide a method and apparatus for folding absorbent sanitary articles that overcome the problems of the prior art.

According to the present invention, this object is achieved by a method and by an apparatus for folding absorbent sanitary articles having the characteristics forming the subject of claims 1 and 6.

Preferred embodiments form the subject of the dependent claims.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

It will be appreciated that the accompanying drawings are schematic and that—in certain figures—some components may not be shown to assist in understanding the Figures. It will be appreciated that the various figures may also not be represented on the same scale.

DETAILED DESCRIPTION

Figure 1:
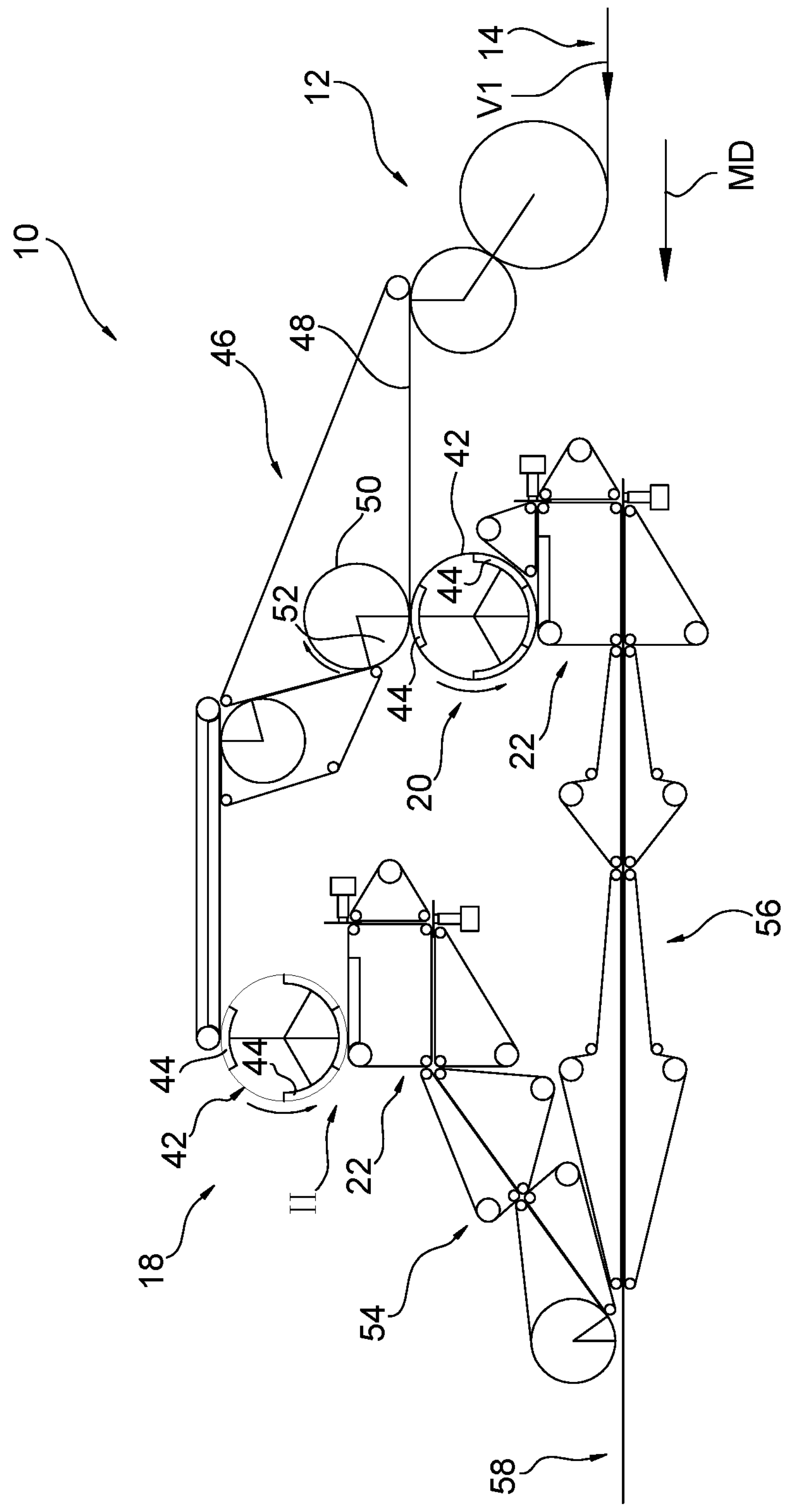
FIG. 1 is a schematic side view of an embodiment of an apparatus for folding absorbent sanitary articles according to the present invention.

With reference to FIG. 1, numeral 10 indicates an apparatus for folding absorbent sanitary articles. The apparatus 10 may be arranged at the outlet of a production machine and upstream of a packaging machine (not shown).

Figures 3A, 3B, 3C, 3D, 3E:
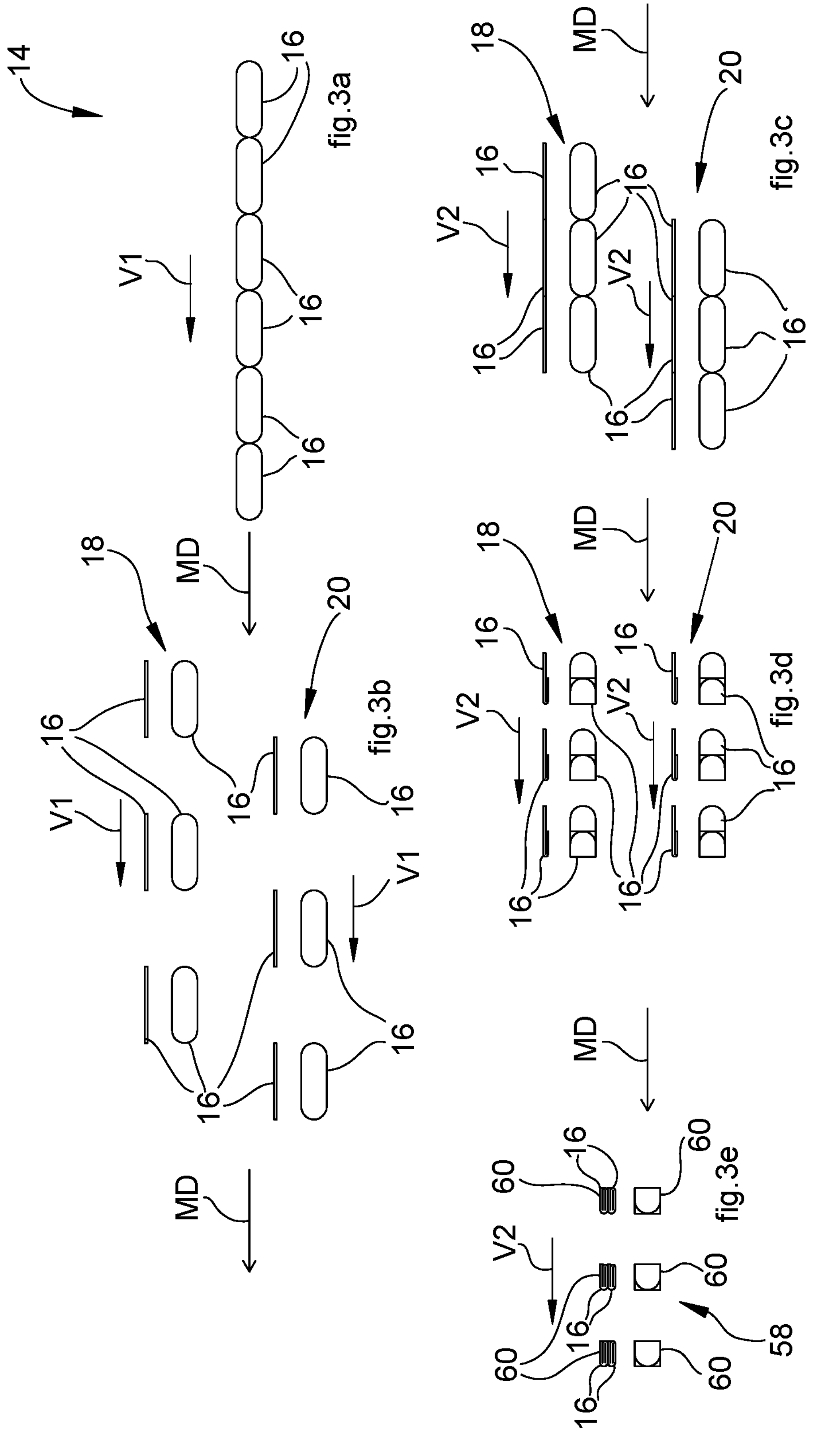

With reference to FIGS. 1 and 3*a*, the apparatus 10 comprises an inlet conveyor 12 configured to advance an inlet array 14 along a machine direction MD at a first speed V1.

The inlet array 14 is formed by a plurality of absorbent sanitary articles 16 aligned with each other. The absorbent sanitary articles 16 forming the inlet array are in the state in which they leave a production machine. In particular, the absorbent sanitary articles 16 in the inlet array 14 are extended in a flat shape and are package-free.

The absorbent sanitary articles 16 in the inlet array 14 have respective longitudinal axes aligned with each other and parallel to the machine direction MD.

In the inlet array 14 the absorbent sanitary articles 16 may be substantially in contact with each other, so that the pitch between the absorbent sanitary articles 16 is substantially equal to their length.

The apparatus 10 comprises at least two folding lines 18, 20 configured to fold the absorbent sanitary articles 16 around respective transversal axes with respect to the longitudinal axes of the absorbent sanitary articles 16.

In the example shown in the figures, the apparatus 10 comprises two folding lines 18, 20. In possible embodiments the apparatus 10 could comprise three or more folding lines.

Each of the folding lines 18, 20 may be configured to fold the absorbent sanitary articles 16 into two or three. When folded in two, the absorbent sanitary articles 16 are folded around a central transversal axis, and after folding have two flaps overlapping each other. When folding in three, the absorbent sanitary articles 16 are folded around two transversal axes located approximately at ⅓ and ⅔ of the length of the absorbent sanitary article 16 and after folding they have three flaps overlapping each other.

Figure 2:
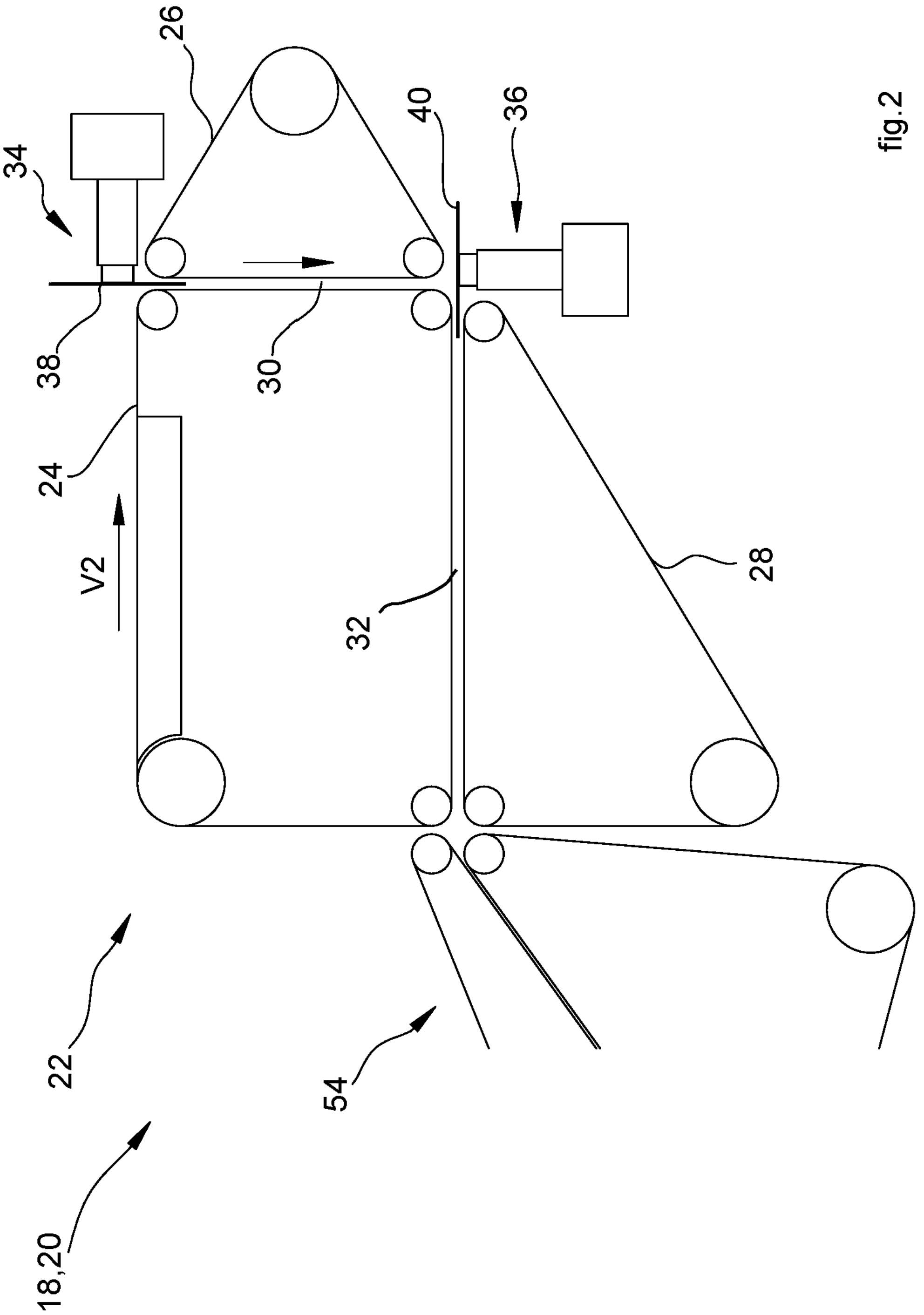
FIG. 2 is a view on an enlarged scale of a folding unit indicated by the arrow II in FIG. 1, FIGS. 3*a*, 3*b*, 3*c*, 3*d*, 3*e* are schematic views illustrating an embodiment of a method for folding absorbent sanitary articles according to the present invention.

With reference to FIG. 2, each folding line 18, 20 may comprise a belt folding device 22. In the shown example, the belt folding device 22 is configured to fold each absorbent sanitary article 16 into three.

The belt folding device 22 comprises a first belt 24, a second belt 26 and a third belt 28. The first belt 24 and the second belt 26 have respective straight sections facing each other which define a first folding channel 30. The first belt 24 and the third belt 28 have respective straight sections facing each other which define a second folding channel 32.

The belt folding device 22 comprises a first inserter device 34 configured to insert successive absorbent sanitary articles 16 into the first folding channel 30, and a second inserter device 36 configured to insert successive absorbent sanitary articles 16 into the second folding channel 32. The first and the second inserting devices 34, 36 may have respective rotating folding blades 38, 40. The absorbent sanitary articles 16 move along the belt folding device 22 in the direction indicated by the arrows and are folded transversely a first time in the first folding channel 30 and a second time in the second folding channel 32.

Each of the folding lines 18, 20 comprises a respective slowing device 42 located upstream of the respective belt folding device 22 and configured to slow down the absorbent sanitary articles 16 which are fed to the belt folding device 22 at a second speed V2 less than the first speed V1.

In this way, in each belt folding device 22 the absorbent sanitary articles 16 are folded while advancing at a speed V2 less than the speed V1 at which the absorbent sanitary articles 16 leave the production machine.

The second speed V2 may be equal to V1/n, where n is the number of folding lines 18, 20.

The slowing device 42 may be a rotating repitch device equipped with a plurality of gripping elements 44 which can rotate independently of each other around a common axis. Each of the gripping elements 44 picks up, for example by suction, an absorbent sanitary article 16 advancing at the speed V1 and releases it to the belt folding device 22 at the second speed V2.

The apparatus 10 comprises a routing device 46 configured to alternatively route the absorbent sanitary articles 16 coming from the inlet array 14 towards the at least two folding lines 18, 20.

In the case wherein the apparatus 10 has two folding lines 18, 20, as in the shown example, the routing device 46 routes an absorbent sanitary article 16 towards the first folding line 18 and the immediately successive absorbent sanitary article 16 towards the second folding line 20, and so on, so that each folding line 18 receives half of the absorbent sanitary articles 16 coming from the inlet array 14.

In the case wherein the apparatus 10 has n folding lines, the routing device 46 routes one absorbent sanitary article 16 to each folding line every n, so that each folding line receives 1/n of the absorbent sanitary articles 16 coming from the inlet array 14.

The routing device 46 may comprise a belt having a branch 48 which retains the absorbent sanitary articles 16 by suction and a transfer wheel 50 provided with one or more suction sectors 52, which alternately transfers the absorbent sanitary articles 16 towards the first folding line 18. The absorbent sanitary articles 16 that are not picked up by the transfer wheel 50 are routed to the second folding line 20.

The folding lines 18, 20 comprise respective outlet conveyors 54, 56 which receive the folded absorbent sanitary articles 16 from the respective belt folding device 22 and feed the folded absorbent sanitary articles 16 into a common outlet array 58.

With reference to FIGS. 3*a*, 3*b*, 3*c*, 3*d*, 3*e*, the operating method of the apparatus 10 is as follows.

In a first step shown in FIG. 3*a*, the method involves forming an inlet array 14 formed by a plurality of absorbent sanitary articles 16 aligned with each other.

The absorbent sanitary articles 16 forming the inlet array 14 in an extended position and without packaging advance along the machine direction MD at the first speed V1.

Then, as shown schematically in FIG. 3*b*, the absorbent sanitary articles 16 coming from the inlet array 14 are routed alternately towards at least two folding lines 18, 20. In FIG. 3*b* and in the successive figures, the absorbent sanitary articles 16 are shown both in plan and in side view.

Subsequently, as shown schematically in FIG. 3*c*, at each of the folding lines 18, 20 the absorbent sanitary articles 16 are slowed down to a second speed V2 less than the first speed V1.

At each folding line 18, 20 the absorbent sanitary articles may be slowed down to the second speed V2 by respective rotating repitch devices 42.

The pitch between the absorbent sanitary articles 16 decreases proportionally to the decrease in speed. For example, if the speed V2 is half the speed V1, the pitch between the absorbent sanitary articles 16 moving at the speed V2 is equal to half the pitch between the same absorbent sanitary articles 16 moving at the speed V1.

In a possible embodiment, at the folding lines 18, 20 the absorbent sanitary articles 16 may advance at different speeds.

Then, as shown schematically in FIG. 3*d*, at each of the folding lines 18, 20 the absorbent sanitary articles 16 are folded around respective transversal axes while advancing at the second speed V2. As already described previously, at each of the folding lines the absorbent sanitary articles 16 may be folded by inserting them into folding channels 30, 32 formed between parallel branches of two belts 24, 26, 28.

The absorbent sanitary articles 16 may be inserted into the folding channels 30, 32 by rotating folding blades 38, 40.

With reference to FIGS. 4*d* and 4*e*, the method involves overlapping the folded absorbent sanitary articles 16 coming from at least two folding lines 18, 20, so as to form groups of articles 60 aligned together in a common outlet array 58.

In particular, the folded absorbent sanitary articles 16 coming from a folding line 18, 20 are overlapped with folded absorbent sanitary articles 16 coming from another folding line 18, 20.

As shown schematically in FIG. 4*d*, the folding lines may feed respective folded absorbent sanitary articles 16 to the common outlet array 58 in phase with each other.

Each of the groups of articles 60 comprises at least two folded absorbent sanitary articles 16 overlapped on each other as shown schematically in FIG. 4*e*.

The groups of articles 60, each of which comprises two or more folded absorbent sanitary articles 16 overlapped on each other, are fed to a packaging unit which encloses each of the groups of articles 60 in a respective packaging film.

Figure 4:
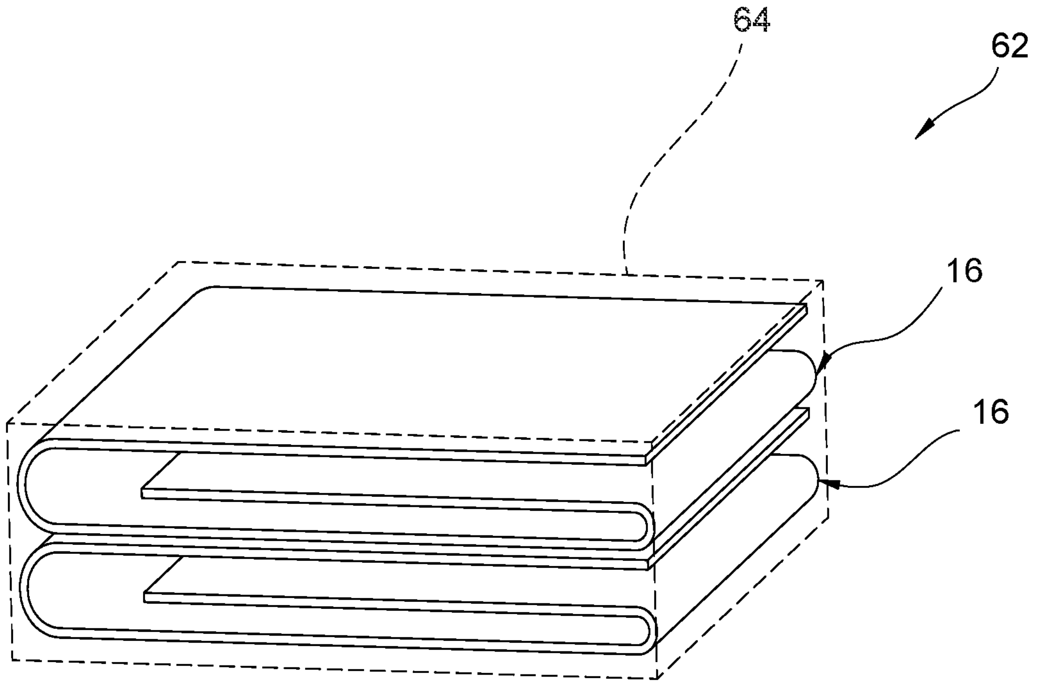
FIG. 4 is a schematic view showing a package obtained with a method and an apparatus according to the present invention.

FIG. 4 illustrates a package 62 obtained with the method. The package comprises two or more folded absorbent sanitary articles 16 overlapped on each other and enclosed in a packaging film 64.

In the common outlet array 58 the folded absorbent sanitary articles 16 may advance at the same speed V2 at which the absorbent sanitary articles advance along the folding lines 18, 20.

The solution according to the present invention allows the folding of the absorbent sanitary articles to be carried out at a lower speed (for example halved) compared to the speed at which the absorbent sanitary articles advance at the end of the production machine. This allows a considerable reduction in the risk of damage to the absorbent sanitary articles.

The solution according to the present invention also allows decreasing (for example halving) the speed of the folded absorbent sanitary articles sent to the packaging unit, without the need to provide belt slowing devices which may lead to the risk of jamming and production stoppages.

Furthermore, the solution according to the present invention allows two or more folded absorbent sanitary articles 16 overlapping each other to be packaged in a single package, which is not generally possible in solutions according to the prior art.

The fact of packaging two or more folded absorbent sanitary articles 16 in a single package allows the number of packages to be reduced for the same number of articles produced.

The apparatus 10 may also be used to individually package the folded absorbent sanitary articles 16 and may switch from single packaging mode to group packaging mode with a selection at the software level, without the need for format change interventions.

Of course, the details of construction and the embodiments can be widely varied with respect to those described and illustrated, without thereby departing from the scope of the present invention as defined by the claims that follow.

The invention claimed is:

1. A method for forming groups of absorbent sanitary articles, comprising:

providing an inlet array formed by a plurality of absorbent sanitary articles, wherein in the inlet array the plurality of absorbent sanitary articles are unpackaged and advance along a machine direction at a first speed, routing the plurality of absorbent sanitary articles coming from said inlet array towards at least two folding lines, at each of said at least two folding lines, slowing down the plurality of absorbent sanitary articles to a second speed and a third speed, respectively, the second speed and the third speed being less than said first speed, at each of said at least two folding lines, folding said plurality of absorbent sanitary articles around respective transversal axes while said plurality of absorbent sanitary articles advance at said respective second and third speeds, overlapping the folded absorbent sanitary articles coming from said at least two folding lines so as to form groups of articles, each of which comprises at least two folded absorbent sanitary articles overlapped on each other, feeding said groups of articles in a common outlet array, and packaging each of said groups of articles in a respective package.

2. The method of claim 1, wherein at said at least two folding lines, said plurality of absorbent sanitary articles advance at speeds different from each other such that said second and third speeds are different from each other.

3. The method of claim 1, wherein said at least two folding lines feed respective folded absorbent sanitary articles towards said common outlet array in phase with each other in the machine direction, so that in said common outlet array the folded absorbent sanitary articles coming from a folding line of said at least two folding lines are overlapped on the folded absorbent sanitary articles coming from another folding line of said at least two folding lines.

4. The method of claim 1, wherein at each of said at least two folding lines, the plurality of absorbent sanitary articles are slowed down to the respective second and third speeds by respective rotating repitch devices.

5. The method of claim 1, wherein at each of said at least two folding lines, the plurality of absorbent sanitary articles are folded by inserting them into folding channels formed between parallel branches of two belts.

6. An apparatus for forming groups of absorbent sanitary articles, comprising:

an inlet conveyor configured to advance an inlet array formed by a plurality of absorbent sanitary articles along a machine direction at a first speed, at least two folding lines each comprising a slowdown device configured to slow down the plurality of absorbent sanitary articles to a second speed and a third speed, respectively, the second speed and the third speed being less than said first speed, wherein said at least two folding lines are configured to fold said plurality of absorbent sanitary articles around respective transversal axes while said plurality of absorbent sanitary articles advance at said respective second and third speeds, a routing device configured to route the plurality of absorbent sanitary articles coming from said inlet array towards said at least two folding lines, wherein said at least two folding lines are configured to feed the folded absorbent sanitary articles into a common outlet array in mutually overlapped positions so as to form in said common outlet array groups of articles each of which comprises at least two folded absorbent sanitary articles overlapped on each other, and a packaging unit in which said groups of articles are packaged in respective packages.

7. The apparatus of claim 6, wherein said at least two folding lines are configured to feed respective folded absorbent sanitary articles to said common outlet array in phase with each other in the machine direction, so that in said common outlet array the folded absorbent sanitary articles coming from a folding line of said at least two folding lines are overlapped with folded absorbent sanitary articles coming from another folding line of said at least two folding lines.

8. The apparatus of claim 6, wherein each of said at least two folding lines comprises a rotary repitch device configured to slow down the plurality of absorbent sanitary articles to the respective second and third speeds.

* * * * *